United States Patent [19]
Speth

[11] 3,974,697
[45] Aug. 17, 1976

[54] METHOD AND APPARATUS FOR SAMPLING A LIQUID STREAM

[75] Inventor: Sebastian Speth, Oberhausen, Germany

[73] Assignee: Ruhrchemi Aktiengesellchaft, Germany

[22] Filed: Oct. 21, 1974

[21] Appl. No.: 516,295

[30] Foreign Application Priority Data
Oct. 29, 1973 Germany............................ 2354091

[52] U.S. Cl.............................. 73/422 R; 141/130
[51] Int. Cl.².......................................... G01N 1/14
[58] Field of Search..... 73/422 GC, 422 TC, 422 R; 141/130, 51

[56] References Cited
UNITED STATES PATENTS

| | | | |
|---|---|---|---|
| 2,268,289 | 12/1941 | Kronquist | 141/51 |
| 3,357,233 | 12/1967 | Roof | 73/422 GC |
| 3,441,066 | 4/1969 | Wilhere | 137/804 |
| 3,545,502 | 8/1967 | Nunlist | 137/804 |
| 3,719,081 | 3/1973 | Lynn | 73/422 R |

Primary Examiner—S. Clement Swisher
Attorney, Agent, or Firm—Bierman & Bierman

[57] ABSTRACT

A method for rapid intermittent sampling of a fluid stream is disclosed. It comprises forming a jet of a part of the stream, diverting the flow of the jet along a first path positioned at an angle to the axis of the jet by forming a pressure differential across the width of the jet, the pressure being lower in the direction of the first path, intermittently redirecting the flow of the jet to a second path by reducing the pressure differential, and sampling the fluid stream when the jet is redirected to the second path.

9 Claims, 1 Drawing Figure

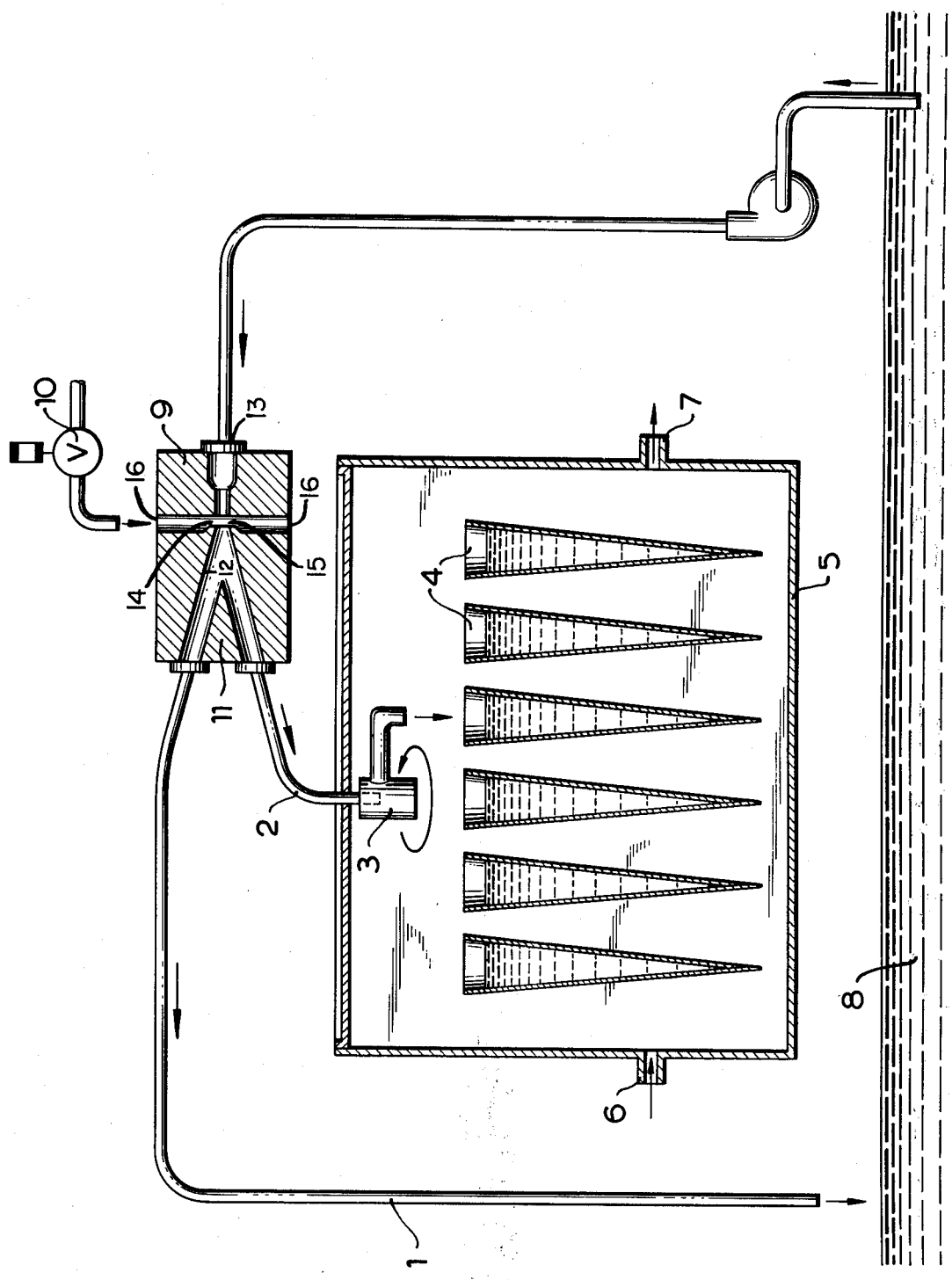

METHOD AND APPARATUS FOR SAMPLING A LIQUID STREAM

Sampling of liquids is often necessary for supervising and monitoring the course and progress of chemical and industrial processes. Moreover, constant chemical and biological water analyses are indispensable in the fields of water conservation, rainfall studies and runoff relations law. For example, continuously or intermittently operating pumps of various designs are known for sampling water (Dr. Hans Günther Goebgen, Cologne, "Messen and automatische Probenahme in der Abwasserkontrolle" [Measuring and automatic sampling in waste water control and supervision], "Unabhaengige Monatszeitschrift fur industrielle Wasserwirtschaft, Luftreinhaltung und Abfallverwertung", Vol. 12 September 1968, No. 9, pgs. 1 to 4). Moreover, samples can be taken from a liquid-directing system by actuating valves for short periods of time. The average values of the property to be studied are determined by analysis of the purified individual samples.

In the case of materials having small variations in its properties, this kind of sampling is sufficient to satisfy statistical laws. Furthermore, the average amount of sample collected can be kept conveniently small. For fouled and contaminated liquids, however, this kind of sampling is unsatisfactory because pumps having a small delivery and periodically actuated valves are readily fouled. For instance, when sampling from industrial waste waters, constituents having particle sizes up to 3 millimeters must be conveyable without hindrance and impediment; See, Goebgen, loc.cit. For this reason, efforts have been made to maintain a greater liquid flow and divert the flowing system for a short period of time to a sampling device. This system which is constructed in the manner of a switch is subject to the laws of mass dynamics. Hence, the duration for the reciprocating switch operation cannot be shortened to less than about one second because of shock to the apparatus. A known device of this construction uses 2-liter bottles as collecting vessels with a pump delivery of 100 liters/hr. (see Aus Industrie und Technik "Wasser, Luft and Betrieb", Vol. 16, No. 7, July, 1972, No. 7294). If the bottle is to be exchanged after periods of two hours, one sampling operation of one second duration can be practically made only after 2 minutes. If the contents of 12 collecting bottles are combined to form a daily average sample, a maximum of 720 individual samples is available.

The necessary number of individual samples can be determined on the basis of statistical laws for the confidence range $u$ of an average value $x$ obtained by sampling in dependence on the scattering $s$; see Table 1.

Table 1

Number of individual samplings necessary with a predetermined scattering a to obtain a statistically significant confidence range u for the mean value

| Confidence coefficient | u/s | | |
|---|---|---|---|
| | 5% | 10% | 20% |
| 68.3 % | 400 | 100 | 27 |
| 95 % | 1,500 | 390 | 98 |
| 99 % | 2,665 | 680 | 175 |

Especially in the case of waste water with its great number of variables and characteristics to be evaluated (pH, content of sedimentary material in suspension, substances which are soluble in petroleum ether, heavy metals, phosphate and nitrate and BSB5 and CBS value), the scattering $s$ of any property reaches or exceeds in most cases the order of magnitude of the mean value $x$, which has the result that a substantially higher frequency of samples than generally expected becomes necessary. Therefore, 100 and more individual samples per hour are necessary and by no means unrealistic. The construction principle of a mechanical switch is not capable of meeting the problem. The same is true of complex organic substances.

The present invention resulted from a study of the problems discussed above, and which concentrated on providing a method and a device for sampling from flowing liquids, which combine an adequate switching frequency and limitation of the amount of sample, insensitivity to contaminants, and corrosion resistance to acidic and basic, inorganic and organic substances. This goal was achieved and constitutes the subject of the present invention.

It was found that a method for intermittent sampling from a liquid stream at a statistically dictated frequency by taking off a portion thereof by means of a periodically actuated valve could be achieved. The valve used is a fluidic-type valve constructed in accordance with the Coanda effect. The desired frequency of quantities and samples is adjusted by periodic opening and closing of air channels through the valve.

Briefly stated, the present invention comprises a method for intermittently sampling a flowing fluid stream comprising the steps of removing at least a portion of the stream and forming it into a jet, directing the flow of the jet along a first path at an angle to the axis of the jet by forming a pressure differential across the width of the jet, the pressure being lower in the direction of the first path intermittently redirecting the flow of the jet to a second path by reducing the pressure differential, and sampling the fluid stream from the jet as it flows through one of the paths.

Instead of a flow switch, a fluidic valve which proved useful in control techniques as wall stream amplifier was employed. It was found that by modifying this valve, liquid entering it can be directed at will be hydrodynamic switching into two discharge channels. Switching is effected without moving parts solely by the directed use of the Coanda effect in which the mass stream is controlled by applying vacuum. As is known, this vacuum is established automatically if, at a small distance from the entering water jet, a wall is arranged at an angle between 15 and 60° with respect to the axis of the jet. Due to the jet impulse, the small space between the jet and the wall is rapidly sucked empty, whereby the jet is diverted and conforms itself to the wall. Thus a pressure differential is established.

If this wall is pierced, and briefly opened to the atmosphere such as by means of a valve, the engagement of the stream with the wall is terminated and the liquid jet flow straightforwardly towards a flow divider. It is possible in this manner, with the bore being closed, to direct the total amount of liquid to a discharge channel and, if the bore is open, to pass part of the liquid into a second discharge channel leading to a sampling device. Oscillograph measurements have shown that it is possible in this manner to achieve sampling periods of 1/10 second and less which permits any sample frequency required by statistics to be realized.

It is possible thus, merely by controlling the opening and closing times of the bore in the wall, at a predetermined frequency depending upon the characteristics of the liquids being analyzed, to take samples sufficiently frequently and in amounts sufficient that significant mean values for all characteristics of the liquid become determinable.

Sampling of proportional amounts can additionally be realized by balancing the duration of switching with the flow rate measured in known manner.

A device for carrying out the method is shown in the accompanying drawing with reference to the example of sampling from a sewer, and represents a preferred embodiment.

The flow directing means comprises a fluidic valve 9 with a flow divider 11, a discharge channel 1 for the liquid stream which is constantly conveyed and which is not needed for sampling, and a discharge line 2 for the liquid samples to be taken. From this discharge line, the liquid is passed to separate collecting vessels 4 by means of a separately actuated sampling means 3 of known design. The flow directing means also comprises a valve 10 by means of which the liquid stream is redirected by periodic opening to the atmosphere. With valve 10 being closed, the liquid runs off via the discharge channel 1 to the flow channel 8. If valve 10 is opened, the liquid passes through discharge lines 1 and 2.

Fluid entering the flow directing means at 13 is formed into a jet which flows past openings 14 and 15 in the direction of flow divider 11. A first path, leading to discharge channel 1 is defined by wall 12 and flow divider 11. Wall 12 is disposed at an angle to the initial axis of the jet. Preferably, this angle is 10 to 60° to the axis of the jet flow.

A bore 16 is provided in the flow directing means 9 for creating and controlling a pressure differential across the width of the jet stream. The bore is open to the atmosphere at its lower end and communicates with valve 10 at its upper end. When valve 10 is closed, the jet creates a partial vacuum or reduced pressure near opening 14, the pressure thereby being lower in the vicinity of wall 12. Thus, the flow of liquid through the flow directing means is directed along the first path along wall 12 and into discharge channel 1.

When valve 10 is opened, the partial vacuum or pressure differential becomes lowered due to the increase in pressure at wall opening 14. When the pressure differential has been thus reduced across the width of the jet, the jet becomes redirected away from the first path, along a second path in the direction of flow divider 11. This permits a portion of the liquid to flow into discharge channel 2 for sampling by sampling means 3.

In practice, sampling means 3 can communicate with either the first or second path. Hence, the first path, along wall 12, could lead to the sampling means, the second path leading to a discharge channel.

It can be seen from the foregoing that with valve 10 open to the atmosphere, the fluid jet moving throught the flow directing means impinges upon flow divider 11 whereupon at least part of the stream passes into the discharge channel 12, and the remainder into discharge channel 1. The portion directed into line 2 is removed to a sampling means 3 as indicated in the drawing.

Alternatively, when valve 10 is closed, opening 14 is isolated from the atmosphere, and the movement of the jet past opening 14 reduces the pressure in the region of the opening This causes the path of the jet to redirect itself along the path defined by wall 12. In this position, substantially the entire jet is returned through discharge channel 1 to flow channel 8.

It can be readily appreciated that the opening and closing of valve 10, by changing the pressure differential across the width of the jet, can be used to direct the jet substantially entirely along wall 12 and into the first flow path or along the second path, whereby a portion of the jet may be sampled.

Imhoff hoppers, which are usual in waste water techniques, are conveniently used as collecting vessels 4.

Imhoff hoppers are funnel-shaped gauge glasses with a hight of 40 cm and a volume of 1 liter having a scale divided in cu.cm in the lower zone. With these special gauge glasses the bottom sediments can be determinated.

The collecting vessels 4 can be conveniently arranged in a chamber 5 which is hermetically sealed against the atmosphere and into which a protective gas can be introduced through a means such as feed line 6 and discharge line 7.

The Coanda valves mentioned above have been described by Wiesner in "Uber die Entwicklung von Wandstrahlelementen und ihre Anwendung in einer Steuerung", Krauskopf-Verlag, 1939.

What is claimed is:

1. A method for intermittently sampling a flowing fluid stream comprising the steps of removing at least a portion of the stream and forming it into a jet having an initial axis, directing the flow of the jet along a first path at an angle of 10 to 60° to the axis of the jet by forming a pressure differential across the width of the jet, the pressure being lower in the direction of the first path, intermittently redirecting the flow of the jet to a second path by reducing the pressure differential one of said paths being directed to a sample collector, said jet being directed to the sample collector for periods of 1/10 second or less.

2. The method of claim 1 in which the fluid stream is sampled when the jet is redirected to the second path.

3. The method of claim 2 in which the flow of the jet is redirected to the second path for a period of time proportional to the flow rate of the fluid stream.

4. Apparatus for the intermittent sampling of a flowing fluid stream comprising a fluid redirecting means through which at least a portion of the fluid stream flows, the redirecting means having a wall therein adjacent the first flow path of the fluid entering the redirecting means and at an angle of 10 to 60° thereto, means for creating a pressure differential across the width of the entering fluid stream in the region of the wall to cause the stream to flow in a second flow path, one of said paths being directed to a sample collector, said fluid redirecting means being operable for periods of 1/10 second or less.

5. Apparatus of claim 4 in which sampling means communicates with the stream when it is flowing in the second direction.

6. Apparatus of claim 5 in which the sampling means further communicates with at least one sample-containing vessel.

7. Apparatus of claim 6 in which the vessel is an Imhoff hopper.

8. Apparatus of claim 6 in which the vessel is positioned in a chamber, said chamber being hermetically sealed and having a protective gas introduction means whereby a protective gas can be introduced into the chamber.

9. Apparatus according to claim 4 wherein said means for creating a pressure differential is a bore with its axis substantially transverse to said path, said bore remaining open to the atmosphere at the end thereof nearest said second direction and said bore being intermittently open to the atmosphere at the end thereof nearest said first direction.

* * * * *